(12) United States Patent
Törmälä et al.

(10) Patent No.: US 6,551,343 B1
(45) Date of Patent: Apr. 22, 2003

(54) BIOABSORBABLE SURGICAL FASTENER FOR TISSUE TREATMENT

(75) Inventors: Pertti Törmälä, Tampere (FI); Markku Tamminmäki, Tampere (FI); Timo Pohjonen, Tampere (FI); Auvo Kaikkonen, Tampere (FI)

(73) Assignee: Bionx Implants, Oy, Tampere (FI)

( * ) Notice: Subject to any disclaimer, the term of this patent is extended or adjusted under 35 U.S.C. 154(b) by 0 days.

(21) Appl. No.: 09/523,869

(22) Filed: Mar. 14, 2000

Related U.S. Application Data

(63) Continuation of application No. 09/053,670, filed on Apr. 1, 1998, now abandoned.

(51) Int. Cl.[7] .............................................. A61B 17/00
(52) U.S. Cl. ...................... 606/213; 606/75; 606/154; 606/155
(58) Field of Search ................................ 606/72, 73, 75, 606/77, 155, 213, 154

(56) References Cited

U.S. PATENT DOCUMENTS

| | | |
|---|---|---|
| 1,206,425 A | 11/1916 | Feasey |
| 1,311,903 A | 8/1919 | Leschander |
| 1,949,111 A | 2/1934 | Randall |
| 2,570,465 A | 10/1951 | Lundholm |
| 2,631,854 A | 3/1953 | Volman |
| 3,123,077 A | 3/1964 | Alcamo |
| 3,166,072 A | 1/1965 | Sullivan |
| 3,236,142 A | 2/1966 | Bradway |
| 3,593,342 A | 7/1971 | Niebauer et al. |
| 3,636,956 A | 1/1972 | Schneider |
| 3,646,615 A | 3/1972 | Ness |
| 3,716,058 A | 2/1973 | Tanner |
| 3,757,629 A | 9/1973 | Schneider |
| 3,867,728 A | 2/1975 | Stubstad et al. |
| 3,892,232 A | 7/1975 | Neufeld |

(List continued on next page.)

FOREIGN PATENT DOCUMENTS

| | | |
|---|---|---|
| DE | 27 40 274 B2 | 4/1980 |
| EP | 0 146 398 | 6/1985 |
| EP | 0317406 | 5/1989 |
| EP | 0 317406 | 5/1989 |
| EP | 0 454 645 | 10/1991 |
| EP | 0 513736 | 11/1992 |
| EP | 0 526 682 | 2/1993 |

(List continued on next page.)

OTHER PUBLICATIONS

Search Report for International Application No. PCT/EP99/02231.

Cato T. Laurencin et al., Use of Polyphosphazenes for Skeletal Tissue Regeneration, Journal of Biomedical Materials Research, vol. 27, pp. 963–973 (1993).

(List continued on next page.)

*Primary Examiner*—Cary E. O'Connor
(74) *Attorney, Agent, or Firm*—Kenyon & Kenyon

(57) ABSTRACT

The present invention relates to a surgical fastener or device (implant) formed in the shape of an arrow comprising a shaft with a proximal (first) portion having a blunt end and tapered form, such that the proximal portion is broad at its blunt end and tapers in the direction of a distal (second) portion of the shaft, the distal portion having protrusions and a pointed end, wherein the tapered form of the proximal portion and the protrusions of the distal portion are configured to lock the implant in a position inside a soft and/or tough tissue according to the use of the implant. The implant may be manufactured of a polymer or a polymeric compound which is substantially (bio)absorbable (resorable) after implantation in tissue and contains an oriented reinforcing structure or the like of a polymer or polymeric compound or ceramic bioactive glass compound.

10 Claims, 6 Drawing Sheets

U.S. PATENT DOCUMENTS

| | | |
|---|---|---|
| 3,946,740 A | 3/1976 | Bassett |
| 3,960,152 A | 6/1976 | Augurt et al. |
| 3,981,051 A | 9/1976 | Brumlik |
| 4,006,747 A | 2/1977 | Kronenthal et al. |
| 4,060,089 A | 11/1977 | Noiles |
| 4,259,959 A | 4/1981 | Walker |
| 4,263,903 A | 4/1981 | Griggs |
| 4,313,232 A | 2/1982 | Habal et al. |
| 4,316,469 A | 2/1982 | Kapitanov |
| 4,402,445 A | 9/1983 | Green |
| 4,451,397 A | 5/1984 | Huc et al. |
| 4,454,875 A | 6/1984 | Pratt et al. |
| 4,532,926 A | 8/1985 | O'Holla |
| 4,548,202 A | 10/1985 | Duncan |
| 4,634,445 A | 1/1987 | Helal |
| 4,635,637 A | 1/1987 | Schreiber |
| 4,655,777 A | 4/1987 | Dunn et al. |
| 4,669,473 A | 6/1987 | Richards et al. |
| 4,688,561 A | 8/1987 | Reese |
| 4,743,257 A | 5/1988 | Tormala et al. ............... 623/16 |
| 4,873,976 A | 10/1989 | Schreiber |
| 4,884,572 A | 12/1989 | Bays et al. ................. 411/510 |
| 4,895,141 A | 1/1990 | Koeneman et al. ........... 606/54 |
| 4,895,148 A | 1/1990 | Bays et al. ................. 606/213 |
| 4,898,186 A | 2/1990 | Ikada et al. .................... 606/62 |
| 4,924,865 A | 5/1990 | Bays et al. .................... 606/77 |
| 4,935,028 A | 6/1990 | Drews ......................... 606/220 |
| 4,968,317 A | 11/1990 | Tormala et al. ............... 606/77 |
| 4,976,715 A | 12/1990 | Bays et al. .................... 606/77 |
| 5,013,316 A | 5/1991 | Goble et al. .................. 606/72 |
| 5,053,047 A | 10/1991 | Yoon .......................... 606/223 |
| 5,059,206 A | 10/1991 | Winters ...................... 606/213 |
| 5,084,051 A | 1/1992 | Tormala et al. ............... 606/77 |
| 5,092,896 A | 3/1992 | Meuli et al. .................. 623/21 |
| 5,102,421 A | 4/1992 | Anspach ..................... 606/232 |
| 5,108,443 A | 4/1992 | Branemark .................. 623/21 |
| 5,129,906 A | 7/1992 | Ross et al. .................... 606/77 |
| 5,201,766 A | 4/1993 | Georgette ................... 623/16 |
| 5,203,864 A | 4/1993 | Philips ........................ 606/151 |
| 5,207,712 A | 5/1993 | Cohen .......................... 623/21 |
| 5,236,431 A | 8/1993 | Gogolewski et al. ......... 606/72 |
| 5,246,441 A | 9/1993 | Ross et al. .................... 606/53 |
| 5,261,914 A | 11/1993 | Warren ........................ 606/73 |
| 5,312,360 A | 5/1994 | Behl ............................ 606/198 |
| 5,370,646 A | 12/1994 | Reese et al. ................... 606/72 |
| 5,374,268 A | 12/1994 | Sander ......................... 606/72 |
| 5,376,118 A | 12/1994 | Kaplan et al. ................ 623/11 |
| 5,398,861 A | 3/1995 | Green ......................... 227/175 |
| 5,425,747 A | 6/1995 | Brotz ........................... 623/13 |
| 5,425,766 A | 6/1995 | Bowald ....................... 623/13 |
| 5,480,447 A | 1/1996 | Skiba .......................... 623/21 |
| 5,505,735 A | 4/1996 | Li ............................... 606/72 |
| 5,507,823 A | 4/1996 | Walston et al. ............... 623/21 |
| 5,514,181 A | 5/1996 | Light et al. ................... 623/13 |
| 5,534,033 A | 7/1996 | Simpson ...................... 623/18 |
| 5,549,676 A | 8/1996 | Johnson ....................... 623/13 |
| 5,562,704 A | 10/1996 | Tamminmaki et al. |
| 5,569,252 A | 10/1996 | Justin et al. .................. 606/73 |
| 5,569,264 A | 10/1996 | Tamminmaki et al. ...... 606/104 |
| 5,643,319 A | 7/1997 | Green ......................... 606/218 |
| 5,683,466 A | 11/1997 | Vitale .......................... 623/18 |
| 5,702,472 A | 12/1997 | Huebner ...................... 623/21 |
| 5,720,766 A | 2/1998 | Zang et al. ................. 606/232 |
| 5,827,298 A | 10/1998 | Hart et al. ................... 606/139 |
| 5,843,084 A | 12/1998 | Hart et al. .................... 606/77 |
| 5,980,524 A | 11/1999 | Justin et al. .................. 606/75 |

FOREIGN PATENT DOCUMENTS

| | | |
|---|---|---|
| EP | 0 592000 | 4/1994 |
| EP | 0592000 | 4/1994 |
| EP | 0 423 155 B1 | 11/1994 |
| EP | 0 632999 | 1/1995 |
| EP | 0632999 | 1/1995 |
| EP | 0 770354 | 5/1997 |
| EP | 0 773 008 | 5/1997 |
| FR | 2 458 275 | 1/1981 |
| FR | 2 712 486 | 5/1995 |
| WO | WO 85 01210 | 3/1985 |
| WO | WO 85/03857 | 9/1985 |
| WO | WO 88 05312 | 7/1988 |
| WO | WO 89 03663 A1 | 5/1989 |
| WO | WO 90 12550 | 11/1990 |
| WO | WO 91 16014 A1 | 10/1991 |
| WO | WO 93 14705 | 8/1993 |
| WO | WO 94 13228 | 6/1994 |
| WO | WO 95 22359 | 8/1995 |
| WO | WO 96 21628 | 7/1996 |
| WO | WO 96 24310 | 8/1996 |
| WO | WO 96 41596 | 12/1996 |
| WO | WO 97/18762 | 5/1997 |

OTHER PUBLICATIONS

Medical Data International, Inc., Orthopedic and Musculoskeletal Markets: Biotechnology and Tissue Engineering, Feb. 1997 at ES 1–18 and 1–28.

N.A. Palmeri et al., The Development and Testing of the Arthroscopic Meniscal Staple, Arthroscopy, vol. 5, No. 2, 1989, p. 156.

S. Vainionpaa et al., Surgical Applications of Biodegradable Polymers in Human Tissues, Progr. Polym. Sci. 14 (1989), pp. 679–716.

Search Report for International Application No. PCT/EP98/03030.

Ashammakhi et al., Strength retention of self–reinforced polyglycolide membrane; an experimental study, Biomaterials 16 (1995), pp. 135–138.

Search Report for PCT/FI 96/00351.

Search Report for Finnish Patent Application 952884.

Sasserath et al., Acta Stomatologica, Belica 88, No. 1 (1991), pp. 5–11 (See English language summary on p. 10).

Search Report for International Counterpart Application PCT/EP98/04183.

Lieutenant Colonel Robert W. Augustine et al., Boat–Nail Fixation of Tendons and Ligaments to Cancellous Bone, The Journal of Bone and Joint Surgery, vol. 38–A, No. 5, Oct. 1956.

Robert W. Augustine, M.D., Repair of the Dislocated Shoulder Using the Modified Magnuson Technic, American Journal of Surgery, vol. 91, May 1956.

Warren Stone Bickham, The Operative Technic Involved in The Operations of General and Specific Surgery, Operative Surgery, vol. II.

Search Report for Counterpart Application PCT/EP/02231.

BIOABSORBABLE SURGICAL FASTENER FOR TISSUE TREATMENT

This application is a continuation of application Ser. No. 09/053,670, filed Apr. 1, 1998, now abandoned.

FIELD OF THE INVENTION

The present invention relates to a surgical fastener or device (implant) formed in the shape of an arrow comprising a shaft with a proximal (first) portion having a blunt end and tapered form, such that the proximal portion is broad at its blunt end and tapers in the direction of a distal (second) portion of the shaft, the distal portion having protrusions and a pointed end, wherein the tapered form of the proximal portion and the protrusions of the distal portion are configured to lock the implant in a position inside a soft and/or tough tissue according to the use of the implant. The implant may be manufactured of a polymer or a polymeric compound which is substantially (bio)absorbable (resorbable) after implantation in tissue and contains an oriented reinforcing structure or the like of a polymer or polymeric compound or ceramic bioactive glass compound.

The surgical implant of the invention is particularly, but not solely, suitable for use in surgically repairing traumas of soft and/or tough tissues containing fibrous structures, such as knee meniscal tissues.

BACKGROUND ART

With reference to the prior art in the field, it has been shown that fixation of meniscus traumas, like ruptures and lesions, by suturing with absorbable sutures gives better results than removal of traumatized meniscal tissue, see e.g. N. A Palmeri, T. F. Winters, A. E. Joiner and T. Evans, "The Development and Testing of the Arthroscopic Meniscal Staple", Arthroscopy, Vol. 5, No. 2, 1989, p. 156, the entire disclosure of which is incorporated herein by reference. However, arthroscopic suturing is a complicated and tedious technique where risks for the patient are significant because of danger to vessels and nerves. Additionally, the suturing of meniscus ruptures leaves a single or several loops of sutures on the meniscal surface, which can irritate joint cavity tissues. Therefore, for a long time surgeons have desired an absorbable meniscus lesion fixation device, like a staple or fastener, which has the advantages of absorbable suturing techniques but which can be used more rapidly and safely than sutures.

Several research groups have tried to develop absorbable meniscus lesion fixation devices, such as clamps. However, the various demands upon such a device are high. It must be strong enough to maintain good contact with the lesion tissues after the operation so that rapid healing occurs, while retaining its strength long enough to ensure good healing. It also must be absorbed without causing complications that would prevent the healing of the lesion. Additionally, the installation of the device should be easy and rapid and should cause minimum operational trauma. Because of these high demands, an optimal absorbable meniscus lesion fixation device has not been developed yet. Palmeri et al., supra, reported the development of a method of meniscal repair using arthroscopically applied absorbable fasteners. However, the reported method was complicated because the final design used cannulation of the staple for needle-guided placement. Additionally, staple fracture, migration and articular abrasion was found.

With regard to implants known in this field, reference is made to U.S. Pat. No. 4,873,976, the entire disclosure of which is incorporated herein by reference, which patent discloses an arrow-like implant particularly intended for the surgical repair of meniscal ruptures. However, the arrow-like implant according to that patent has the disadvantage that its proximal end (stem) is shaped as a plate in a way that the direction of the main plane of the plate is perpendicular to the longitudinal direction of the arrow's body. Because of this fact, it is particularly difficult to install the implant, because the channel used to install the implant must have the cross-sectional shape of the stem; thus, it is difficult to guide the implant in the installation channel, because the guiding effect is substantially brought upon the stem only, but not the body of the arrow due to its shape. Furthermore, the structure of the stem causes tissue irritation and abrasion, particularly when placed in connection with the meniscus because the stem is usually left protruding to a high degree from the outer surface of the meniscus.

Bays et al. (U.S. Pat. Nos. 4,884,572 and 4,895,141, the entire disclosures of which are incorporated herein by way of this reference) describe a surgical-repair tack and applicator and method of using them. The tack has a barb member, a shaft portion and a grip portion. The tack is made of biodegradable material having a degradation time selected to coincide with the healing time of the tissue. In an alternative embodiment, the tack's barb comprises a continuous helical barb. A disadvantage of this tack is that the grip portion is bulky and may remain on the meniscal surface, causing irritation inside a joint cavity.

The method and apparatus for repairing a meniscal tear disclosed by Winters (U.S. Pat. No. 5,059,206, the entire disclosure of which is incorporated herein by way of this reference) comprises a fastener having protrusions or barbs that is applied to a meniscal tear with a delivery device. The delivery device has a flexible tip that is manipulable through a curved radius to enable the surgeon to insert the device into the central part of the knee and then extend the fastener radially outward into and across a meniscal tear. Also in this case, the proximal end of the fastener is bulky comprising a cylindrical end (head member) which protrudes partially above and/or below the outer surface of the meniscus.

Tamminmäki et al. (U.S. Pat. No. 5,562,704, the entire disclosure of which is incorporated herein by way of this reference) disclose an arrow-like bioabsorbable implant particularly intended for the surgical repair of meniscal ruptures. This implant does not have the guiding or abrasion problems that the implants of U.S. Pat. No 4,873,976 or U.S. Pat. No. 5,059,206 may have. However, a disadvantage of the device of U.S. Pat. No. 5,562,704 is that the proximal part of the implant (the wings) preferably remains on the surface of the meniscus, so that when the wings break as a consequence of bioabsorption, the broken wings may irritate knee joint tissues. Moreover, if the proximal part with the wings is desired to be located inside of meniscal tissue, the surface capsule of the meniscus must be cut horizontally with a special cutting blade. This lengthens the operation time and causes substantial damage to the meniscus surface.

U.S. Pat. No. 5,569,252, the entire disclosure of which is incorporated herein by way of this reference, describes a fastener, an installation device, and method for repairing tears in the soft tissue of a patient, including meniscal tears. The fastener has a variable-pitch helical protrusion along a central portion that decreases from the distal end to the proximal end, which can serve to bring two sides of the tear into opposition as the fastener is advanced across the two sides of the tear in a screwing motion. This implant, which needs a screwing motion for installation, is slow and tedious to use arthroscopically and the turning of the implant through fibrous tissue, such as meniscus tissue, has the risk that the fibrous tissue may twist around the turning implant, hindering or preventing the installation of the implant.

Orthopedic and Musculoskeletal Markets Biotechnology and Tissue Engineering, Medical Data International, Inc., Irvine, Calif. USA, February 1997, p. 1–17, the entire disclosure of which is incorporated herein by way of this reference, describes a bioabsorbable device for meniscal repair. This device has two legs with molded barbs that are attached by a flexible member composed of resorbable suture. The device is installed into a meniscus with an arthroscopic tool, so that the legs penetrate the rupture of the meniscus to hold the edges together. The disadvantage of this device is that the suture loop remains on the surface of meniscus where it can cause irritation. Additionally, this two-leg device requires a bulky installation tool which makes arthroscopic installation of the device difficult.

U.S. patent application Ser. No. 08/887,130, the entire disclosure of which is incorporated herein by way of this reference, describes a fastener for body tissue repair comprising: a shaft comprised of a proximal portion, having an upper surface and a lower surface with first protrusions, and a distal portion, said distal portion having a sharpened tip and one or more first protrusions, wherein said first protrusions have proximal surfaces configured to arrest the movement of the shaft in the proximal direction and distal surfaces configured to permit the movement of the shaft in the distal direction, said proximal portion having second protrusions on the upper surface and lower surface of the proximal portion, wherein said second protrusions have distal surfaces configured to arrest the movement of the shaft in the distal direction. Although this implant sinks totally inside a tissue,-like a knee meniscus, the second protrusions can be damaged, e.g., bent or broken, during the insertion of the implant into tissue, or the second protrusions can damage the tissue, e.g., by cutting the horizontal collagen fibers of the tissue during the insertion.

SUMMARY OF THE INVENTION

Therefore, it is an object of the present invention to provide a bioabsorbable fastener that allows a minimally invasive method for repairing a tear in soft or tough tissue.

It is a further object of the invention to provide such a fastener that is rapid and easy to install and gives a strong and safe fixation of the tissue tear and that may be made from a nontoxic, biocompatible bioabsorbable polymer, polymer alloy or fiber reinforced polymer composite, specially designed to maintain its structural integrity during the healing of the tear and to prevent tissue abrasion. It is an additional object to provide such a fastener having a shape designed to compress the tear.

It is a further object of the invention to provide a device (fastener) which will be shot or pushed totally inside of soft or tough tissue, like meniscal tissue, to penetrate the tissue (meniscal) tear and to hold the ruptured edges together and to cause a minimal trauma to the tissue through which the fastener forces its way. These and other objects are attained with the fastener of the present invention.

The fastener of the present invention is designed for repairing a tear in soft and/or tough tissue of a patient, such as a tear of the meniscus within the knee. The surgical fastener or device (implant) of the present invention has been formed in the shape of an arrow comprising a shaft with a proximal (first) portion having a blunt end and tapered form so that the blunt end of the proximal portion is broad and it tapers in the direction of a distal (second) portion of the shaft, the distal portion having protrusions and a pointed end, the tapered form of the proximal portion and the protrusions of the distal portion configured to lock the implant in a position inside a soft and/or tough tissue according to use of the implant. Accordingly, protrusions emerge from the distal portion of the device. The protrusions are typically barbs, scales, threads, serrations, ridges or the like. These protrusions at the distal portion of the shaft of the device prevent the installed device from slipping out of the meniscal tissue in the direction opposite to the direction of installation. At least one or more of the protrusions must penetrate the rupture plane inside of the tissue, to lock the distal portion of the device into the tissue at a position distal of the tear. The tapered form of the proximal portion of the shaft allows the penetration of the shaft into the meniscal tissue when the fastener is pushed, shot or hammered into the tissue. Because of the tapered structure, the penetration of the proximal portion of the shaft into the meniscal tissue causes minimal damage, because the penetrating, tapered proximal portion does not cut the horizontal collagen fibers of meniscal tissue, but separates them from each other when the proximal portion forms a cavity for itself in the meniscal tissue. The opening of such a cavity inside of meniscal tissue for the tapered proximal portion requires a substantial amount of external pushing force from the installation device, which pushes the fastener into the meniscal tissue. When the fastener is totally inside of the meniscus and the pushing force is ended, the fastener stops inside of the meniscal tissue and the tapered proximal portion prevents the further penetration of the fastener into the meniscal tissue. In this way, the combined effect of the distal protrusions and the proximal tapered portion lock the fastener effectively inside of the meniscus, to close and fix the meniscal rupture to enhance its healing.

In a preferred embodiment of the present invention, the protrusions of the distal portion of the shaft of the device are formed so that they facilitate the slipping of the device into the meniscus during insertion, while resisting the slipping of the device in the direction opposite to the installation direction. On the other hand, the tapered proximal portion of the shaft of the device is formed so that it stops the device inside of the meniscal tissue when the device has been pushed or shot into the meniscus with the delivery (installation) tool. Both distal protrusions and the proximal tapered portion of the device of the invention, acting together, exert an advantageous compression on the ruptured surface when the device of the invention is shot into the meniscus and across the rupture. This compression serves to close the rupture and promotes healing.

A further advantageous feature of the device is that the surface of the shaft may include longitudinal ridges. The ridges promote healing of the rupture by providing channels along the interiors of the ridges through which beneficial blood flow can occur along the length of the device. These channels, which are typically about 0.05–0.5 mm wide, act as capillaries, transporting blood from the highly vascularized distal portion (outer periphery) of the meniscus to the poorly vascularized proximal portion (inner periphery) of the meniscus. Further, the ridges help to guide the fastener through the cannula of the installation instrument and into the meniscal or other soft tissue during installation.

BRIEF DESCRIPTION OF THE DRAWINGS

FIGS. 3A–3G illustrate, seen from the proximal end of the fastener, different proximal end profiles of fasteners in accordance with the invention.

FIGS. 11–12 illustrate the orientation of the fibrous structure of the meniscus in relation to an installed fastener of the invention.

DETAILED DESCRIPTION OF THE PREFERRED EMBODIMENTS

Figure 1A:
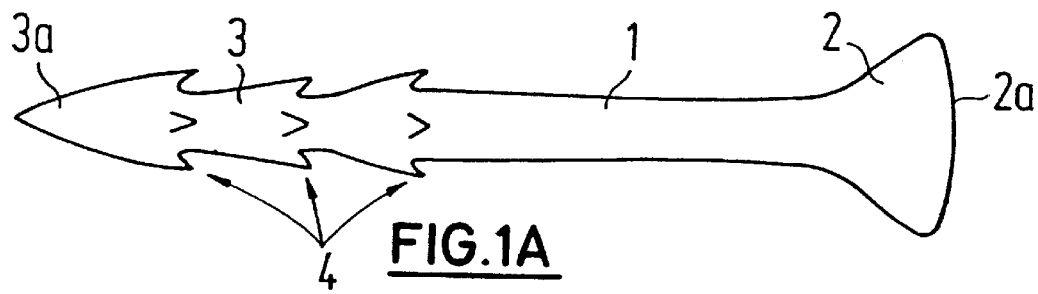
FIGS. 1A–1E illustrate, seen from above, fasteners (devices) in accordance with the invention.

A description of the preferred embodiments of the present invention is presented with reference to FIGS. 1–12.

The preferred exemplary embodiment of the present invention comprises a fastener and method for repairing a soft or tough tissue, like a knee meniscal tear, in a human patient. FIGS. 1A–1E illustrate, as viewed from above, some preferred embodiments of the fastener. It is designed to have an arrow shape, and it comprises a shaft 1, whose proximal portion 2 is formed with a blunt end 2a for the purpose of providing the impact surface required for the instrument used in its installation (delivery tool), and whose distal portion 3 is formed with a head with a sharp tip 3a. The distal portion comprises distal protrusions 4 with respect to the shaft 1. The distal protrusions depicted in FIGS. 1A–1E are small, sharp-profile barbs. The purpose of the proximal portion 2 is to stop the implant inside of the meniscus, typically just below the surface of the meniscus during the final stage of the installation. To achieve this task, the proximal portion 2 is formed tapered with maximum width near the blunt end 2a, so that the tapered end stops the device and prevents.its further sinking into the meniscus, when the pushing effect of the delivery tool stops.

Figure 1B:
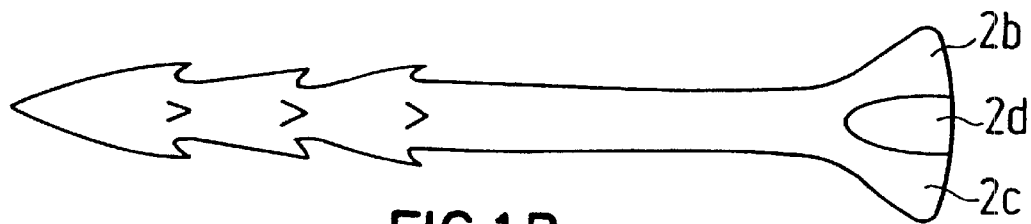
Figure 1C:
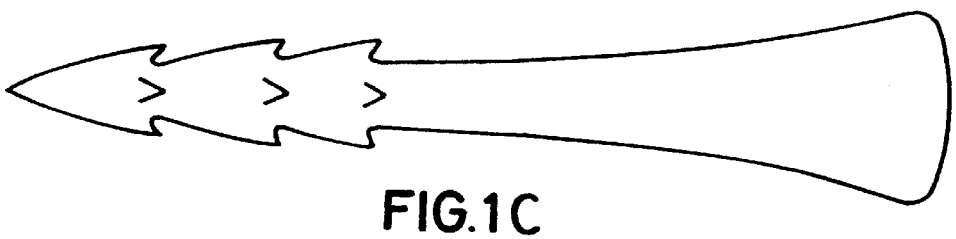
Figure 1D:
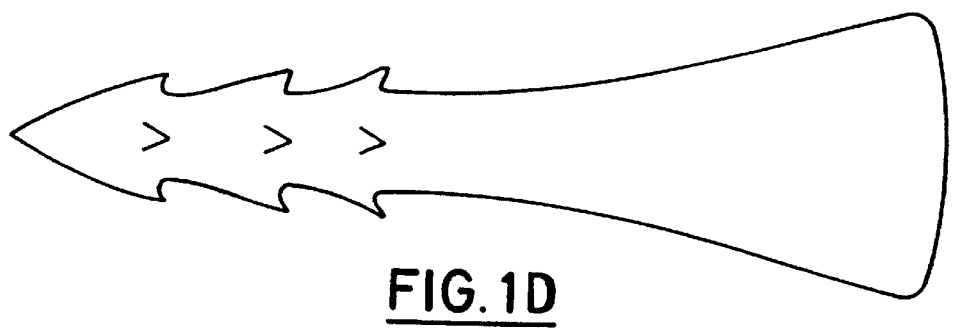
Figure 1E:
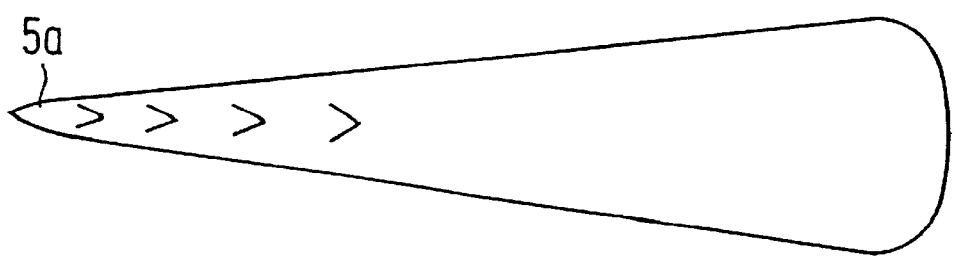
Figure 2A:
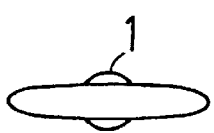
FIG. 2 illustrates a ridged fastener in accordance with the invention.
Figure 2B:
Figure 2C:
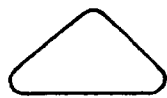
Figure 2D:
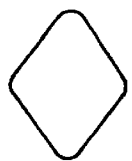
Figure 2E:
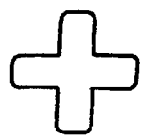
Figure 2F:
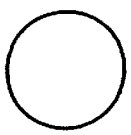
Figure 2G:
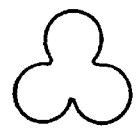

As shown in FIGS. 1A–1E, the tapering effect of the device can be varied and can extend to different distances from the proximal end of the fastener along the shaft 1. In the extreme case, as shown in FIG. 1E, the tapering reaches to the tip 5a of the wedge-like fastener. The tapered proximal portion 2 may have different cross-sectional geometries. Some preferred embodiments are described in FIG.2, where, seen from the proximal end of the fastener, different proximal end profiles are described. According to FIG. 2A the proximal portion is flat. Such a flat proximal portion penetrates into meniscal tissue causing only a minimal disturbance to the internal structure of the meniscus. However, because the proximal end of the proximal portion is broader than the width of the shaft 1, the flat and broad proximal portion stops the fastener effectively inside of the meniscal tissue. According to FIG. 2B, the flat proximal portion can have a thicker midsection, advantageously even thicker than the diameter d of shaft 1. The thickening of the tapered proximal portion increases its locking effect inside of meniscal tissue. FIGS. 2C and 2D show proximal portions with a triangular and a quadrangular cross-section, respectively. FIG. 2E shows a proximal portion with a cross-like cross-section. This kind of proximal portion is also seen in FIG. 1B, with two arms of the cross-like proximal portion 2b and 2c lying flat in the plane of the figure and with the third arm 2d protruding up from the plane of the figure. FIG. 2F shows the circular cross-section of a (conical) proximal portion. FIG. 2G describes the cross-sectional geometry of a proximal portion comprising three tapering ridges.

Accordingly, the proximal tapered portion 2 and distal protrusions 4 effectively lock the device inside of the meniscus preventing, after insertion, its movement both in the direction of installation and in the direction opposite to it. Additionally, the installation of the device serves to advantageously compress the rupture surface (see FIGS. 8A–D) because the proximal tapered portion 2 pushes the proximal side of the rupture against the distal side of the rupture during the final phase of installation.

Because the whole device is located inside of the meniscus and the tapered proximal portion forces itself into the meniscus without cutting the horizontal collagen fibers, the complications and risks that could otherwise originate from (a) the presence of the proximal part of the device on the meniscal surface or (b) the cutting of collagen fibers by the first (proximal) protrusions, as in the prior art devices, are eliminated.

Figure 3A:
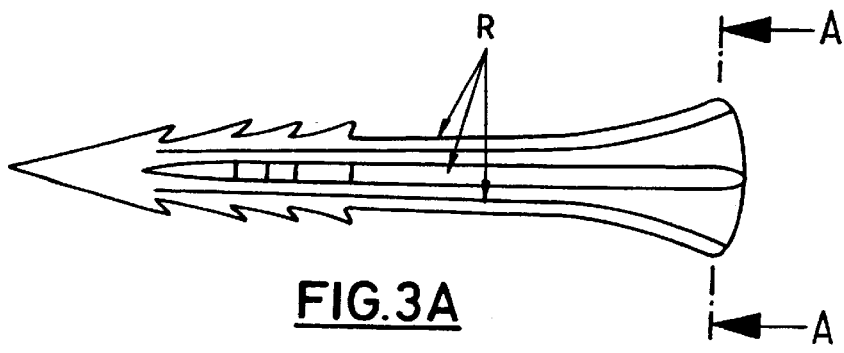
Figure 3B:
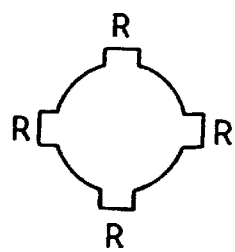
Figure 4:
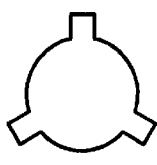
FIGS. 4–7 describe different ridge profiles of fasteners in accordance with the invention.
Figure 4:
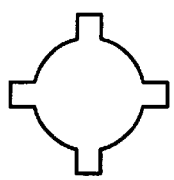
Figure 4:
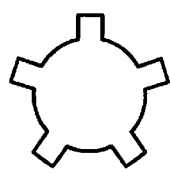
Figure 4:
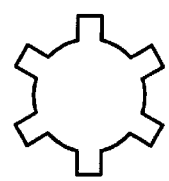
Figure 4:
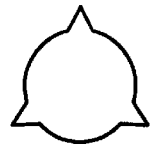
Figure 4:
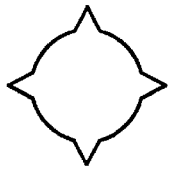
Figure 4:
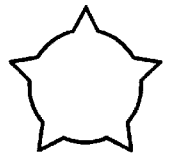
Figure 4:
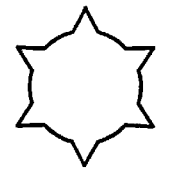
Figure 5:
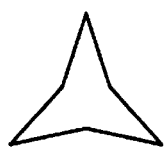
Figure 5:
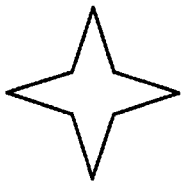
Figure 5:
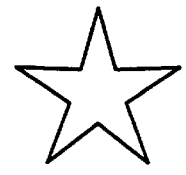
Figure 5:
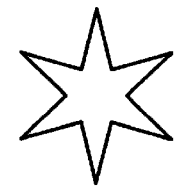
Figure 5:
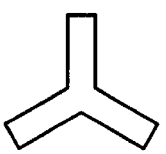
Figure 5:
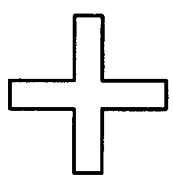
Figure 5:
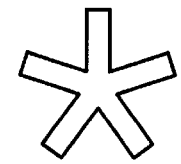
Figure 5:
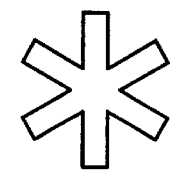
Figure 6:
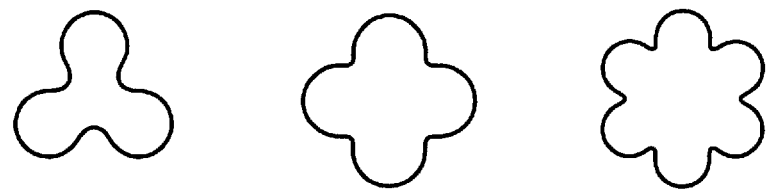
Figure 7:
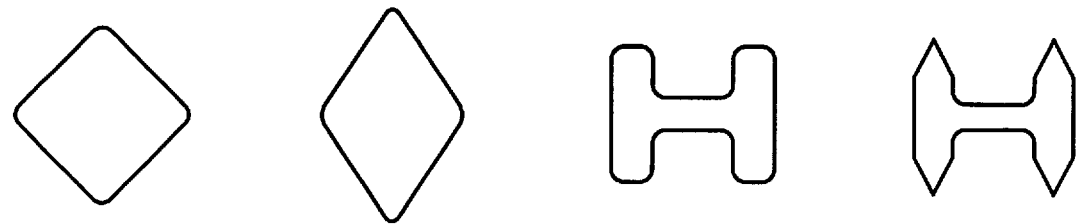

The surface of the fastener can also include longitudinal ridges, into which the arresting means (proximal tapered portion and distal protrusions) can be machined or molded. FIG. 3A shows a side-view perspective of such a fastener having on its surface four longitudinal ridges 13, which are arranged onto the surface of the fastener according to FIG. 3B, which shows the cross-section of the fastener in the plane A—A of FIG. 3A. The distal protrusions (e.g., barbs) can be machined effectively into the longitudinal ridges.

It is evident that other types of distal protrusions, than those described in FIG. 1 and 3, can be used in the fasteners of the invention. Such protrusions are described, e.g., in U.S. patent application Ser. No. 08/887,130, the entire disclosure of which is incorporated herein by way of this reference.

Likewise, there are numerous possible arrangements for the longitudinal ridges on the surface of the fastener. Also the geometry of the ridges can be varied to influence the gripping capacity of the protrusions and of the tapered proximal end inside of the meniscal or other soft tissue. FIGS. 4–7 illustrate some preferred embodiments of the cross-sectional structures of ridged fasteners.

Figure 8A:
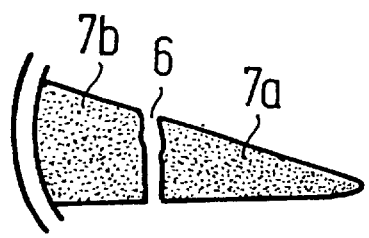
FIGS. 8A–D illustrate a cross-section of the installation of the fastener of the invention into a torn meniscus.
Figure 8B:
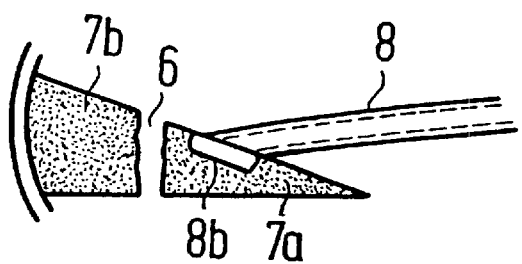
Figure 8C:
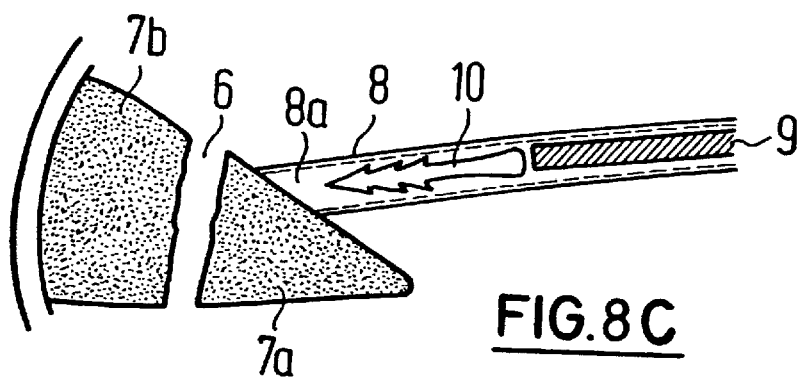
Figure 8D:
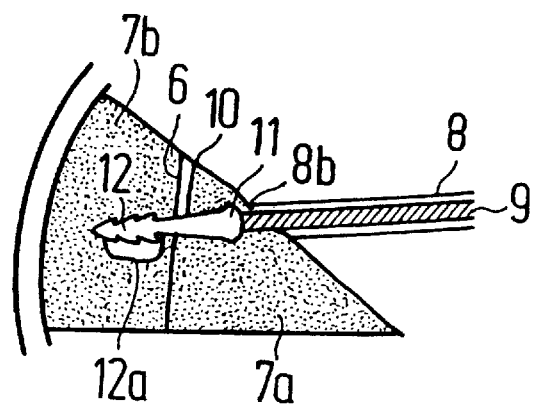
Figure 9:
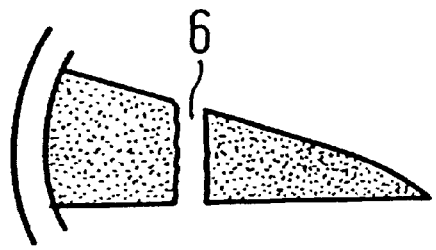
FIGS. 9–10 illustrate the fibrous structure of the meniscus for repair.

FIGS. 8A–D illustrate a preferred method for installing fasteners of the invention into ruptured meniscal tissue. FIG. 8A illustrates, as viewed from the side, a meniscus with a rupture, 6, separating the meniscus into a proximal side, 7a, and a distal side, 7b. As shown through FIG. 8B, during the operation, the tip 8b of a cannula 8 is pushed into the knee joint through a small incision and the tip is located on the surface of the proximal part of the meniscus 7a (in relation to the rupture 6). As seen in FIG. 8C, the piston 9 moves to the left (distally) and pushes the fastener 10 through the hole 8a inside of the cannula 8. The piston 9 can be accelerated to a high speed so that the piston 9 pushes (shoots) the fastener 10 with a high speed into the meniscus as is illustrated in FIG. 8D. The piston 9 stops at the final stage of its movement (by way of, e.g., a stopper (not shown) at the proximal end of the piston 9), typically so that the tip of the piston 9 protrudes out of the tip 8b of the cannula 8 about 0.5–1 mm, thus pushing the fastener totally inside of the meniscal tissue. When the location of the cannula tip 8b on the meniscal surface is selected in an appropriate manner, typically 2–4 mm in front of the meniscal tear 6, and the direction of the cannula is proper, the fastener penetrates the proximal meniscus part 7a and the tear plane 6, and closes the tear with the compression force created by the pushing force of the installation. According to FIG. 8D, the piston 9 pushes and forces the fastener 10 totally inside of the meniscal tissue. When the tapered proximal portion 11 of the fastener is forced inside of the meniscal tissue (see FIG. 8D), it imparts the pushing force into the proximal part of the meniscus 7a, thereby closing the rupture 6. As soon as the piston 9 stops (typically 0.5–1 mm below the surface of the meniscus) the proximal tapered portion 11 stops the fastener and prevents its further movement into the meniscal tissue. On the other hand, the distal portion of the device 12 is pushed across the rupture 6 and into the distal side of the meniscus 7b, where the distal protrusions 12a prevent the slipping of the fastener back in the direction opposite to the installation direction. Accordingly, the rupture 6 is closed effectively, the fastener is locked into its position to keep the rupture 6 closed, and the whole fastener has been buried with minimal damage inside of the meniscal tissue, thus eliminating the risks related to prior art implants that have parts located on the surface of the meniscus.

It is typical that the microstructure of a meniscus contains reinforcing collagen fibers. Inside of a meniscus, many collagen fibers are oriented in a horizontal plane nearly parallel to the lower surface of the meniscus. If the horizontal collagen fibers are examined in a cut cross-section of a meniscus (as shown in FIGS. 8A–D) their cut ends can be seen microscopically as points on the cross-sectional surface, according to FIG. 9. The typical vertical meniscus lesion (rupture) 6 develops along the long axes of collagen fibers, because the secondary (e.g., hydrogen) binding forces between collagen fibers are weaker than the primary covalent bonds along the long axis of fibers.

Figure 10:
Figure 11:
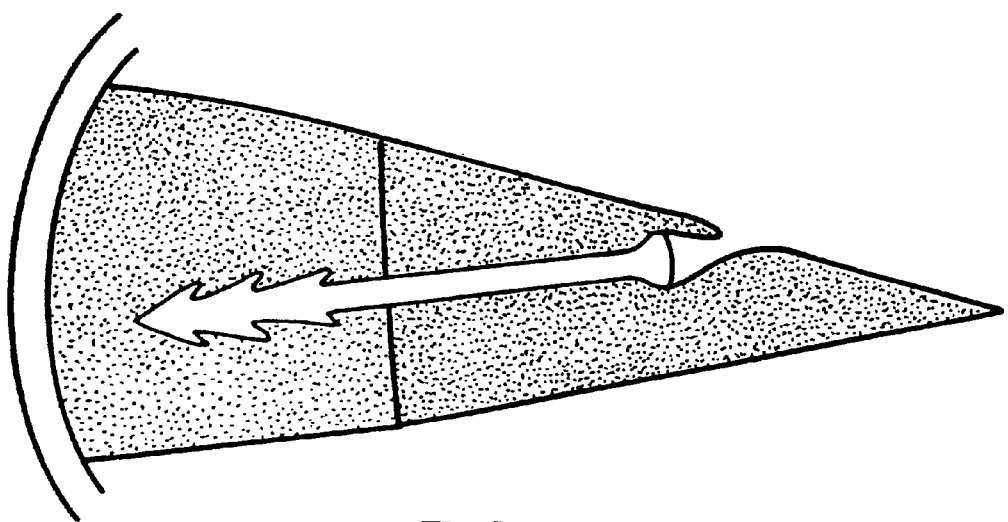

If the internal collagen fiber structure of a meniscus is examined from the direction of the long axis of the fastener, i.e., from the direction from which the fastener enters the meniscus, the horizontal collagen fibers are seen as parallel, horizontal fiber bundles, as is shown schematically in FIG. 10. Because of the special arrangement of the main portion of reinforcing horizontal collagen fibers inside of the meniscus, shown schematically in FIGS. 9 and 10, it is important that the distal protrusions are located at least on the upper and lower surfaces of the distal portion of the fastener, so that as the fastener penetrates into the meniscal tissue, the distal protrusions slide forward through the collagen fiber bundles and ultimately grip between the horizontal collagen fiber bundles, locking the fastener in place. On the other hand, it is important that the proximal portion is tapered and broadened in the direction of its proximal end so that it locks the proximal portion into place inside of the meniscus, when the pushing effect of the installation device is ended. This arrangement of an installed fastener of the invention is shown schematically in FIG. 11 as a meniscal cross-section.

It is well known that a typical meniscus also includes oriented fibers that are not horizontal. For example, the meniscus can also contain fibers having radial or oblique orientations. The collagen fibers form an essentially three-dimensional network in the meniscus, with such fibers being of particular importance with regard to using the present invention for treating the typical vertical (bucket handle) tears that occur. For example, even if most of the collagen fibers are oriented horizontally, some of the fibers will have other orientations (e.g., vertical), such that when the device of the invention enters the resultant three-dimensional network of collage fibers it will not slip out or through that network.

The bioabsorbable implants of this invention can be manufactured of bioabsorbable polymers, copolymers or polymer mixtures or alloys with melt molding methods known in the prior art. It is also possible to use the techniques of U.S. Pat. No. 4,743,257, the entire disclosure of which is incorporated herein by reference, to mold (in a compression or injection mold) absorbable fibers and binding polymer together to create a fiber-reinforced or especially a self-reinforced structure. The implants of this invention can be molded in a single compression molding cycle, or the protrusions can be machined on the surface of a fastener after the molding cycle.

The oriented and/or self-reinforced structure of the material used to make the invention can also be created during extrusion or injection molding of an absorbable polymeric melt, through a suitable die or into a suitable mold at high speed and pressure. When cooling occurs at suitable conditions, the flow orientation of the melt remains at least partially intact in the solid material as an oriented or self-reinforcing structure. Such suitable conditions include rapid cooling to a temperature well below the melting point of the polymeric material, to lock the desired orientation into the material used to make the invention. In an advantageous embodiment, the mold can have the form of the implant, but it is also possible to manufacture the implants of the invention by machining (optionally, using heat) injection-molding or extruding semi-finished products.

It is advantageous to make the implants of melt-molded, solid state drawn or compressed, bioabsorbable polymeric materials, which are described e.g. in U.S. Pat. Nos. 4,968,317 or 4,898,186, the entire disclosures of both of which are incorporated herein by way of this reference.

The reinforcing fibers of the implant can also be ceramic fibers, like bioabsorbable hydroxyapatite or bioactive glass fibers. Such bioabsorbable, ceramic fiber reinforced materials are described e.g. in European Patent Application No. 0146398 and in WO 96/21628, the entire disclosures of which are incorporated herein by way of this reference.

The oriented and/or self-reinforced or otherwise fiber reinforced implants of this invention can be manufactured by molding the reinforcement fiber-polymer matrix to the final product in a mold, whose mold cavity has the form of the final product, or the final form can be machined mechanically (optionally also using heat) on a preform, such as a melt-molded and solid-state drawn rod, as is described e.g. in U.S. Pat. No. 4,968,317.

In some advantageous embodiments of this invention, the orientation and/or reinforcing elements of the self-reinforced structure are mainly oriented in the direction of the long axis of the shaft of the implant. The reinforcement elements may extend into any protrusions or ridges of the implant. The reinforcements elements can also turn spirally around the long axis of the implant. Also, other different orientations of reinforcement elements in elongated samples which are known and familiar from composite technology can be applied to the present invention. However, a general feature of orientation and/or fiber-reinforcement or self-reinforcement of the implants of this invention is that many of the reinforcing elements are oriented in such a way that they can carry the different external loads (such as tensile, bending and shear loads) that are directed to the healing rupture (for example loads to a meniscus caused by the movements of the patient's knee).

According to an advantageous embodiment of the invention, the meniscal repair implant, or an optional bioabsorbable, polymeric coating layer on its surface, may contain one or more bioactive substances, such as antibiotics, chemotherapeutic substances, angiogenic growth factors, substances accelerating the healing of the wound, growth hormones and the like. Such bioactive meniscal repair implants are especially advantageous in surgical use, because they chemically contribute to the healing of the lesion in addition to providing mechanical support.

The oriented and/or reinforced materials of the implants typically have tensile strengths of around 100–2000 MPa, bending strengths of around 100–600 MPa and shear strengths of around 80–400 MPa. Additionally, they are usually stiff and tough. These mechanical properties are superior to those of non-reinforced absorbable polymers which typically show strengths between 40 and 100 MPa and are additionally either very flexible or brittle (see e.g. Ref. 3 S. Vainionpää, P. Rokkanen and P. Törmälä, "Surgical Applications of Biodegradable Polymers in Human Tissues", Progr. Polym. Sci 14/1989, pp. 679–716, the entire disclosure of which is incorporated herein by way of this reference).

The implants of the present invention may be sterilized by any of the well known sterilization techniques, depending on the type of material used in manufacture of the implant. Suitable sterilization techniques include heat or steam sterilization, radiation sterilization, such as cobalt 60 irradiation or electron beams), ethylene oxide sterilization, and the like.

After the above description of the present invention and certain specific embodiments thereof, it will be readily.apparent to those skilled in the art that many variations and modifications may be made to the present invention without departing from the, spirit and scope thereof.

We claim:

1. A fastener for soft tissue or meniscus repair comprising: a tapered, single shaft having a proximal portion having a first width and a distal portion having a second width, wherein said first width is greater than said second width and the tapered, single shaft tapers from the proximal portion toward the distal portion, said distal portion having one or more protrusions, said protrusions having proximal surfaces configured to arrest the movement of the fastener in the proximal direction and distal surfaces configured to permit the movement of the fastener in the distal direction, wherein said proximal portion of said tapered, single shaft is capable of permitting the movement of the fastener in the distal direction until said fastener is pushed to a desired point inside the soft tissue or meniscus to be repaired and said tapered, single shaft and protrusions are capable of locking said fastener inside said tissue to be repaired, and further comprising one or more longitudinal ridges disposed on the shaft between the distal portion and the proximal portion of the fastener.

2. A fastener according to claim 1, wherein said distal protrusions are disposed on said one or more longitudinal ridges.

3. A fastener according to claim 1, further comprising a bioactive material disposed in the fastener.

4. A method for the repair of a rupture in a meniscus having a surface, using the fastener of claim 1, said method comprising the steps of:

aligning the fastener of claim 1 on the surface of the meniscus; and pushing the fastener into the meniscus so that the fastener is embedded within the meniscus and bridges the rupture.

5. A fastener according to claim 1, said fastener is manufactured from a bioabsorbable material.

6. A fastener according to claim 5, wherein said protrusions comprise barbs.

7. A fastener according to claim 5, further comprising one or more longitudinal ridges disposed on the shaft between the distal portion and the proximal portion of the fastener.

8. A fastener according to claim 7, wherein said distal protrusions are disposed on said one or more longitudinal ridges.

9. A fastener according to claim 8, further comprising a bioactive material disposed in the fastener.

10. A method for the repair of a tear in a meniscus using the fastener of claim 5, said method comprising the steps of:

aligning the fastener of claim 5 on a surface of the meniscus; and pushing the fastener into the meniscus and across the tear in the meniscus, so that the tapered shaft and protrusions of the fastener lock the fastener inside the meniscus and close the tear in the meniscus.

* * * * *